United States Patent
Holman

(10) Patent No.: US 10,732,778 B2
(45) Date of Patent: Aug. 4, 2020

(54) BIOMETRIC SENSOR

(71) Applicant: Tactual Labs Co., New York, NY (US)

(72) Inventor: David Holman, Toronto (CA)

(73) Assignee: Tactual Labs Co., New York, NY (US)

( * ) Notice: Subject to any disclaimer, the term of this patent is extended or adjusted under 35 U.S.C. 154(b) by 0 days.

(21) Appl. No.: 16/102,185

(22) Filed: Aug. 13, 2018

(65) Prior Publication Data

US 2019/0050082 A1 Feb. 14, 2019

Related U.S. Application Data

(63) Continuation-in-part of application No. 15/943,221, filed on Apr. 2, 2018, and a continuation-in-part of application No. 15/904,953, filed on Feb. 26, 2018, now Pat. No. 10,620,696.

(60) Provisional application No. 62/657,120, filed on Apr. 13, 2018, provisional application No. 62/657,270, filed on Apr. 13, 2018, provisional application No. 62/621,117, filed on Jan. 24, 2018, provisional application No. 62/588,267, filed on Nov. 17, 2017, provisional application No. 62/588,148, filed on Nov. 17, 2017, provisional application No. 62/473,908, filed on Mar. 20, 2017, provisional application No. 62/488,753, filed on Apr. 22, 2017, provisional application No. 62/533,405, filed on Jul. 17, 2017.

(51) Int. Cl.
| | |
|---|---|
| *G06F 3/044* | (2006.01) |
| *A61B 5/00* | (2006.01) |
| *G06F 3/041* | (2006.01) |
| *A61B 5/05* | (2006.01) |
| *G06K 9/00* | (2006.01) |

(52) U.S. Cl.
CPC ............ *G06F 3/044* (2013.01); *A61B 5/0507* (2013.01); *A61B 5/681* (2013.01); *A61B 5/6802* (2013.01); *G06F 3/0416* (2013.01); *A61B 5/6806* (2013.01); *G06F 2203/04102* (2013.01); *G06F 2203/04104* (2013.01); *G06K 9/00885* (2013.01); *G06K 2009/00939* (2013.01)

(58) Field of Classification Search
CPC .................. G06F 3/044; G06F 3/0416; G06F 2203/04102; G06F 2203/04104; G06K 9/00885; G06K 2009/00939; A61B 5/681; A61B 5/0507; A61B 5/6802; A61B 5/6806
USPC ..................................... 73/777, 779
See application file for complete search history.

(56) References Cited

U.S. PATENT DOCUMENTS

| | | | | |
|---|---|---|---|---|
| 6,307,471 B1 * | 10/2001 | Xydis | ..................... | G06F 21/35 340/539.1 |
| 7,109,933 B2 * | 9/2006 | Ito | ..................... | A61B 1/00016 343/718 |
| 8,065,163 B2 * | 11/2011 | Morita | ................... | G06Q 10/10 705/2 |
| 9,035,775 B2 * | 5/2015 | Margon | ................. | A61B 5/024 340/573.1 |
| 9,520,638 B2 * | 12/2016 | Baringer | ................ | H01Q 21/28 |

(Continued)

*Primary Examiner* — Octavia Hollington

(74) *Attorney, Agent, or Firm* — Adam B. Landa

(57) ABSTRACT

A biometric sensing apparatus is employed by a person in order to obtain biometric data. Transmitting and receiving antennas are used in order to transmit and receive signals. Measurements of the received signals are correlated with biological activity in order to provide biometric data.

25 Claims, 4 Drawing Sheets

(56) References Cited

U.S. PATENT DOCUMENTS

| | | | |
|---|---|---|---|
| 9,734,315 B2* | 8/2017 | Seol | G06F 3/03547 |
| 2007/0066904 A1 | 3/2007 | Wiesmann et al. | |
| 2013/0245436 A1 | 9/2013 | Tupin, Jr. et al. | |
| 2014/0316261 A1* | 10/2014 | Lux | A61B 5/0022 |
| | | | 600/430 |
| 2014/0378809 A1* | 12/2014 | Weitnauer | G01S 13/50 |
| | | | 600/407 |
| 2015/0018676 A1 | 1/2015 | Barak | |
| 2015/0320336 A1 | 11/2015 | Tao et al. | |
| 2016/0174842 A1* | 6/2016 | Hyde | A61B 5/0031 |
| | | | 342/52 |
| 2016/0294599 A1 | 10/2016 | Feher | |
| 2017/0119318 A1* | 5/2017 | Shay | A61B 5/05 |
| 2018/0024667 A1* | 1/2018 | Moseley | G06F 3/044 |
| | | | 345/174 |
| 2018/0059819 A1* | 3/2018 | Moseley | G06F 3/016 |

* cited by examiner

BIOMETRIC SENSOR

This application is a continuation-in-part of U.S. patent application Ser. No. 15/943,221 entitled "Flexible Deformation Sensor," filed Apr. 2, 2018. This application also claims the benefit of U.S. Provisional Patent Application No. 62/657,120 entitled "Interior Sensing," filed Apr. 13, 2018. This application also claims the benefit of U.S. Provisional Patent Application No. 62/657,270 entitled "Displacement Sensing to Localize Movement," filed Apr. 13, 2018. This application also is a continuation-in-part of U.S. patent application Ser. No. 15/904,953 entitled "Apparatus and Method for Sensing Deformation," filed Feb. 26, 2018, which in turn claims the benefit of U.S. Provisional Patent Application No. 62/621,117 entitled "Matrix Sensor with Receive Isolation," filed Jan. 24, 2018; U.S. Provisional Patent Application No. 62/588,267 entitled "Sensing Controller," filed on Nov. 17, 2017; and U.S. Provisional Patent Application No. 62/588,148 entitled "Systems and Methods for Infusion Range Sensor," filed on Nov. 17, 2017; U.S. Provisional Patent Application No. 62/473,908 entitled "Hand Sensing Controller," filed Mar. 20, 2017; U.S. Provisional Patent Application No. 62/488,753 entitled "Heterogenous Sensing Apparatus and Methods," filed on Apr. 22, 2017; U.S. Provisional Patent Application No. 62/533,405 entitled "Apparatus and Methods for Enhancing Digit Separation and Reproduction," filed on Jul. 17, 2017. The contents of all the aforementioned applications hereby incorporated herein by reference.

FIELD

The disclosed apparatus and methods relate to the field of sensing, and in particular to sensing used to provide biometric data.

BRIEF DESCRIPTION OF THE DRAWINGS

The foregoing and other objects, features, and advantages of the disclosure will be apparent from the following more particular description of embodiments as illustrated in the accompanying drawings, in which reference characters refer to the same parts throughout the various views. The drawings are not necessarily to scale, emphasis instead being placed upon illustrating principles of the disclosed embodiments.

DETAILED DESCRIPTION

Figure 1:
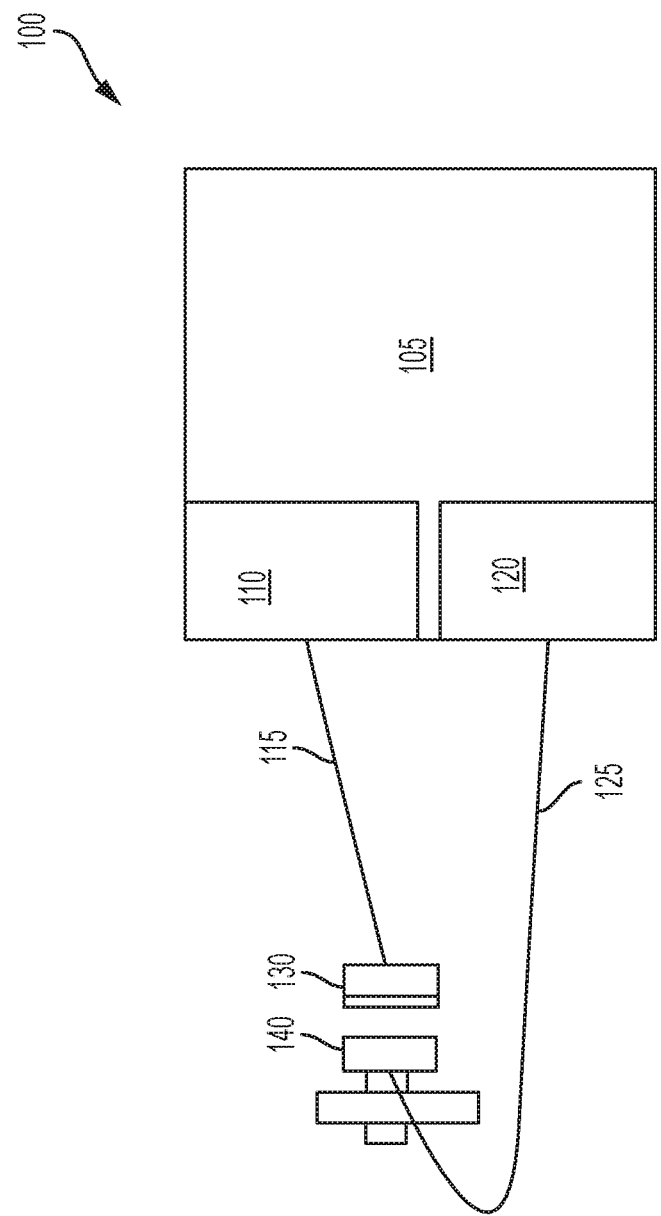
FIG. 1 shows a diagram of a sensing apparatus.

The present application contemplates various embodiments of sensors designed for obtaining biometrics. The sensor configurations are suited for use with frequency-orthogonal signaling techniques (see, e.g., U.S. Pat. Nos. 9,019,224 and 9,529,476, and U.S. Pat. No. 9,811,214, all of which are hereby incorporated herein by reference). The sensor configurations discussed herein may be used with other signal techniques including scanning or time division techniques, and/or code division techniques. It is pertinent to note that the sensors described and illustrated herein are also suitable for use in connection with signal infusion (also referred to as signal injection) techniques and apparatuses.

The presently disclosed systems and methods involve principles related to and for designing, manufacturing and using capacitive based sensors, and particularly capacitive based sensors that employ a multiplexing scheme based on orthogonal signaling such as but not limited to frequency-division multiplexing (FDM), code-division multiplexing (CDM), or a hybrid modulation technique that combines both FDM and CDM methods. References to frequency herein could also refer to other orthogonal signal bases. As such, this application incorporates by reference Applicants' prior U.S. Pat. No. 9,019,224, entitled "Low-Latency Touch Sensitive Device" and U.S. Pat. No. 9,158,411 entitled "Fast Multi-Touch Post Processing." These applications contemplate FDM, CDM, or FDM/CDM hybrid touch sensors which may be used in connection with the presently disclosed sensors. In such sensors, interactions are sensed when a signal from a row is coupled (increased) or decoupled (decreased) to a column and the result received on that column. By sequentially exciting the rows and measuring the coupling of the excitation signal at the columns, a heatmap reflecting capacitance changes, and thus proximity, can be created.

This application also employs principles used in fast multi-touch sensors and other interfaces disclosed in the following: U.S. Pat. Nos. 9,933,880; 9,019,224; 9,811,214; 9,804,721; 9,710,113; and 9,158,411. Familiarity with the disclosure, concepts and nomenclature within these patents is presumed. The entire disclosure of those patents and the applications incorporated therein by reference are incorporated herein by reference. This application also employs principles used in fast multi-touch sensors and other interfaces disclosed in the following: U.S. patent application Ser. Nos. 15/162,240; 15/690,234; 15/195,675; 15/200,642; 15/821,677; 15/904,953; 15/905,465; 15/943,221; 62/540,458, 62/575,005, 62/621,117, 62/619,656 and PCT publication PCT/US2017/050547, familiarity with the disclosures, concepts and nomenclature therein is presumed. The entire disclosure of those applications and the applications incorporated therein by reference are incorporated herein by reference.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristic. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency-orthogonal to each other, in which case, they could not be the same frequency.

Certain principles of a fast multi-touch (FMT) sensor have been disclosed in patent applications discussed above. Orthogonal signals are transmitted into a plurality of transmitting conductors (or antennas) and the information received by receivers attached to a plurality of receiving conductors (or antennas), the signal is then analyzed by a signal processor to identify touch events. The transmitting conductors and receiving conductors may be organized in a variety of configurations, including, e.g., a matrix where the crossing points form nodes, and interactions are detected at those nodes by processing of the received signals. In an embodiment where the orthogonal signals are frequency orthogonal, spacing between the orthogonal frequencies, $\Delta f$, is at least the reciprocal of the measurement period $\tau$, the measurement period $\tau$ being equal to the period during which the columns are sampled. Thus, in an embodiment, a column may be measured for one millisecond ($\tau$) using frequency spacing ($\Delta f$) of one kilohertz (i.e., $\Delta f=1/\tau$).

In an embodiment, the signal processor of a mixed signal integrated circuit (or a downstream component or software) is adapted to determine at least one value representing each frequency orthogonal signal transmitted to a row. In an embodiment, the signal processor of the mixed signal integrated circuit (or a downstream component or software) performs a Fourier transform to received signals. In an embodiment, the mixed signal integrated circuit is adapted to digitize received signals. In an embodiment, the mixed signal integrated circuit (or a downstream component or software) is adapted to digitize received signals and perform a discrete Fourier transform (DFT) on the digitized information. In an embodiment, the mixed signal integrated circuit (or a downstream component or software) is adapted to digitize received signals and perform a Fast Fourier transform (FFT) on the digitized information—an FFT being one type of discrete Fourier transform.

It will be apparent to a person of skill in the art in view of this disclosure that a DFT, in essence, treats the sequence of digital samples (e.g., window) taken during a sampling period (e.g., integration period) as though it repeats. As a consequence, signals that are not center frequencies (i.e., not integer multiples of the reciprocal of the integration period (which reciprocal defines the minimum frequency spacing)), may have relatively nominal, but unintended consequence of contributing small values into other DFT bins. Thus, it will also be apparent to a person of skill in the art in view of this disclosure that, the term orthogonal as used herein is not "violated" by such small contributions. In other words, as we use the term frequency orthogonal herein, two signals are considered frequency orthogonal if substantially all of the contribution of one signal to the DFT bins is made to different DFT bins than substantially all of the contribution of the other signal.

In an embodiment, received signals are sampled at least 1 MHz. In an embodiment, received signals are sampled at at least 2 MHz. In an embodiment, received signals are sampled at 4 Mhz. In an embodiment, received signals are sampled at 4.096 Mhz. In an embodiment, received signals are sampled at more than 4 MHz.

To achieve kHz sampling, for example, 4096 samples may be taken at 4.096 MHz. In such an embodiment, the integration period is 1 millisecond, which per the constraint that the frequency spacing should be greater than or equal to the reciprocal of the integration period provides a minimum frequency spacing of 1 KHz. (It will be apparent to one of skill in the art in view of this disclosure that taking 4096 samples at e.g., 4 MHz would yield an integration period slightly longer than a millisecond, and not achieving kHz sampling, and a minimum frequency spacing of 976.5625 Hz.) In an embodiment, the frequency spacing is equal to the reciprocal of the integration period. In such an embodiment, the maximum frequency of a frequency-orthogonal signal range should be less than 2 MHz. In such an embodiment, the practical maximum frequency of a frequency-orthogonal signal range should be less than about 40% of the sampling rate, or about 1.6 MHz. In an embodiment, a DFT (which could be an FFT) is used to transform the digitized received signals into bins of information, each reflecting the frequency of a frequency-orthogonal signal transmitted which may have been transmitted by the transmit antenna 130. In an embodiment 2048 bins correspond to frequencies from 1 KHz to about 2 MHz. It will be apparent to a person of skill in the art in view of this disclosure that these examples are simply that, exemplary. Depending on the needs of a system, and subject to the constraints described above, the sample rate may be increased or decreased, the integration period may be adjusted, the frequency range may be adjusted, etc.

In an embodiment, a DFT (which can be an FFT) output comprises a bin for each frequency-orthogonal signal that is transmitted. In an embodiment, each DFT (which can be an FFT) bin comprises an in-phase (I) and quadrature (Q) component. In an embodiment, the sum of the squares of the I and Q components is used as measure corresponding to signal strength for that bin. In an embodiment, the square root of the sum of the squares of the I and Q components is used as measure corresponding to signal strength for that bin. It will be apparent to a person of skill in the art in view of this disclosure that a measure corresponding to the signal strength for a bin could be used as a measure related to biometric activity. In other words, the measure corresponding to signal strength in a given bin would change as a result of some activity.

Generally, as the term is used herein, injection or infusion refers to the process of transmitting signals to the body of a subject, effectively allowing the body (or parts of the body) to become an active transmitting source of the signal. In an embodiment, an electrical signal is injected into the hand (or other part of the body) and this signal can be detected by a sensor even when the hand (or fingers or other part of the body) are not in direct contact with the sensor's touch surface. To some degree, this allows the proximity and orientation of the hand (or finger or some other body part) to be determined, relative to a surface. In an embodiment, signals are carried (e.g., conducted) by the body, and depending on the frequencies involved, may be carried near the surface or below the surface as well. In an embodiment, frequencies of at least the KHz range may be used in frequency injection. In an embodiment, frequencies in the MHz range may be used in frequency injection. To use infusion in connection with FMT as described above, in an embodiment, an infusion signal can be selected to be orthogonal to the drive signals, and thus it can be seen in addition to the other signals on the sense lines.

The sensing apparatuses discussed herein use transmitting and receiving antennas (also referred to herein as conductors). However, it should be understood that whether the transmitting antennas or receiving antennas are functioning as a transmitter, a receiver, or both depends on context and the embodiment. In an embodiment, the transmitters and receivers for all or any combination of the patterns are operatively connected to a single integrated circuit capable of transmitting and receiving the required signals. In an embodiment, the transmitters and receivers are each operatively connected to a different integrated circuit capable of transmitting and receiving the required signals, respectively.

In an embodiment, the transmitters and receivers for all or any combination of the patterns may be operatively connected to a group of integrated circuits, each capable of transmitting and receiving the required signals, and together sharing information necessary to such multiple IC configuration. In an embodiment, where the capacity of the integrated circuit (i.e., the number of transmit and receive channels) and the requirements of the patterns (i.e., the number of transmit and receive channels) permit, all of the transmitters and receivers for all of the multiple patterns used by a controller are operated by a common integrated circuit, or by a group of integrated circuits that have communications therebetween. In an embodiment, where the number of transmit or receive channels requires the use of multiple integrated circuits, the information from each circuit is combined in a separate system. In an embodiment, the separate system comprises a GPU and software for signal processing.

Turning to FIG. 1, shown is a diagram of an embodiment of a sensing apparatus 100. In an embodiment, a mixed signal integrated circuit 105 with signal processing capabilities comprises a transmitter 110 and a receiver 120. In an embodiment, an analog front end comprising a transmitter (or multiple transmitters) and a receiver (or multiple receivers) is used to send and receive signals instead of the mixed signal integrated circuit 100. In such an embodiment, the analog front end provides a digital interface to signal generating and signal processing circuits and/or software.

The transmitter 110 is conductively coupled to transmitting antenna 130 via transmit lead 115, and the receiver 120 is conductively coupled to the receiving antenna 140 via receive lead 125. A signal is emitted from the transmitting antenna 130. The signal received by the receiving antenna 140 is measured by the sensing apparatus 100. The amount of signal measured is used in order to provide information about the environment in which it is being used. Movement between the transmitting antenna 130 and the receiving antenna 140 impacts measurements of the signal received by the receiving antenna 140. Additionally, other environmental conditions may impact the measurements made. For example, moisture may impact the measurement of the signal received by the receiving antenna 140.

In an embodiment, the mixed signal integrated circuit 105 is adapted to generate one or more signals and send the signals to the transmitting antennas 130 via the transmitter 110. In an embodiment, the mixed signal integrated circuit 105 is adapted to generate a plurality of frequency-orthogonal signals and send the plurality of frequency-orthogonal signals to the transmit antennas 130. In an embodiment, the mixed signal integrated circuit 105 is adapted to generate a plurality of frequency-orthogonal signals and one or more of the plurality of frequency-orthogonal signals to each of a plurality of transmit antenna. In an embodiment, the frequency-orthogonal signals are in the range from DC up to about 2.5 GHz. In an embodiment, the frequency-orthogonal signals are in the range from DC up to about 1.6 MHz. In an embodiment, the frequency-orthogonal signals are in the range from 50 KHz to 200 KHz. The frequency spacing between the frequency-orthogonal signals should be greater than or equal to the reciprocal of the integration period (i.e., the sampling period).

In an embodiment, the mixed signal integrated circuit 105 (or a downstream component or software) is adapted to determine at least one value representing each frequency orthogonal signal transmitted by a transmit antenna 130. In an embodiment, the mixed signal integrated circuit 105 (or a downstream component or software) performs a Fourier transform received signals. In an embodiment, the mixed signal integrated circuit 105 is adapted to digitize received signals. In an embodiment, the mixed signal integrated circuit 10 (or a downstream component or software) is adapted to digitize received signals and perform a discrete Fourier transform (DFT) on the digitized information. In an embodiment, the mixed signal integrated circuit 100 (or a downstream component or software) is adapted to digitize received signals and perform a Fast Fourier transform (FFT) on the digitized information.

Figure 2:
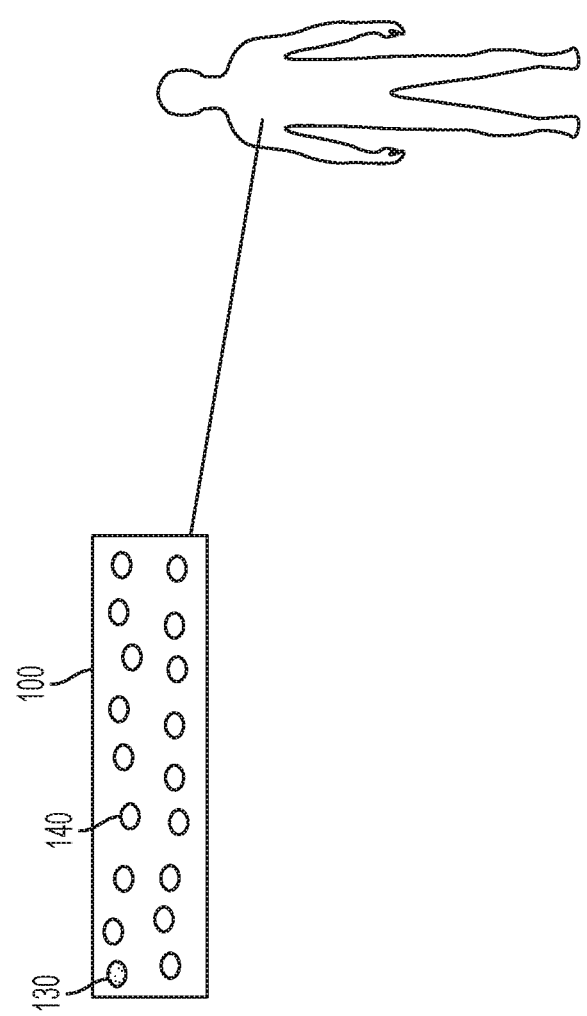
FIG. 2 shows a diagram of a sensing apparatus used with a person.

Turning to FIG. 2, an embodiment of the sensing apparatus 100 is shown that is able to be placed on or in proximity to a portion of the body of a person or animal. In an embodiment, the sensing apparatus 100 comprises a transmitting antenna 130 and a receiving antenna 140. In an embodiment, the sensing apparatus 100 comprises a transmitting antenna 130 and a plurality of receiving antennas 140. In an embodiment, the sensing apparatus 100 comprises a plurality of transmitting antennas 130 and a receiving antenna 140. In an embodiment, the sensing apparatus 100 comprises one or more transmitting antennas 130 and one or more receiving antennas 140. In an embodiment, the sensing apparatus 100 is embedded or encased in a wearable. In an embodiment, the sensing apparatus 100 is suitable to be attached to or applied to the body. In an embodiment, the sensor apparatus 100 comprises an adhesive side that may be applied to the body. In an embodiment, the sensor apparatus 100 is part of or embedded within an article that can be worn such as a wristband, a headband, a neck band, a belt or other such article. In an embodiment, the sensor apparatus 100 is part of or embedded in an article of clothing that is worn in proximity to the skin such as a glove, a shirt, pants, socks or an undergarment.

In an embodiment, a sensing apparatus 100 is formed from two parts (not shown), wherein one part comprises one or more transmitting antennas and another part comprises one or more receiving antennas 140. In an embodiment, the two parts of the sensing apparatus are each worn on the body, e.g., a wristband and a forearm band; or a wristband for the left arm and a wristband for the right arm.

In an embodiment, the transmitting and receiving antenna 130, 140 are conductive. In an embodiment, when the sensing apparatus 100 is located in operational proximity to a subject (e.g., person or animal), the transmitting antenna 130 and receiving antenna 140 are in direct contact with the subject. In an embodiment, when the sensing apparatus 100 is located in operational proximity to a subject (e.g., person or animal), at least one of the transmitting antenna(s) 130 and the receiving antenna(s) 140 are not in direct contact with the subject. In an embodiment, when the sensing apparatus 100 is located in operational proximity to a subject (e.g., person or animal), one or more transmitting or receiving antenna(s) 130, 140 are maintained at a distance from the subject. In an embodiment, such a distance is maintained by a non-conductive coating on the antenna. In an embodiment, such a distance is maintained by a dielectric layer between the antenna and the subject.

In an embodiment, when the sensing apparatus 100 is located in operational proximity to a subject (e.g., person or animal), at least one transmitting antenna 130 is maintained in close proximity to the subject, and at least one receiving antenna 140 is supported on a rigid substrate, for example, supported by a plastic bracelet. In an embodiment, when the sensing apparatus 100 is located in operational proximity to a subject (e.g., person or animal), at least one transmitting antenna 130 is maintained in close proximity to the subject, and a plurality of receiving antennas 140 care supported on a rigid substrate, for example, supported by a plastic bracelet. In an embodiment, when the sensing apparatus 100 is located in operational proximity to a subject (e.g., person or animal), one or more transmitting or receiving antenna(s) 130, 140 are maintained in fixed position with respect to each other, and do not move with the surface of the skin, such as, for example, antennas that remain in position with respect to a bracelet. In an embodiment, when the sensing apparatus 100 is located in operational proximity to a subject (e.g., person or animal), one or more transmitting or receiving antenna(s) 130, 140 are supported on a rigid substrate, for example, antennas that are supported by a plastic bracelet. In an embodiment, when the sensing apparatus 100 is located in operational proximity to a subject (e.g., person or animal), one or more transmitting or receiving antenna(s) 130, 140 are supported on a highly flexible substrate, for example, antennas that are supported on a soft fabric or flexible rubber; and in an embodiment, a soft fabric or flexible rubber substrate may be temporarily affixed to a subject using an adhesive (e.g., like the sticky part of a band aid). In an embodiment, when the sensing apparatus 100 is located in operational proximity to a subject (e.g., person or animal), one or more transmitting or receiving antenna(s) 130, 140 are supported on a flexible substrate, for example, antennas that are supported by a fabric or rubber substrate; in an embodiment, such substrate may resemble a silicone bracelet, or could resemble the non-sticky part of a band aid, which is generally localized by the adhesive part, but will not move precisely with the skin.

In an embodiment, a sensing apparatus comprises a plurality of conductive antennas disbursed on one or more wearable components. In an embodiment, a wearable component is configured such that its antennas are in direct contact with the subject. In an embodiment, a wearable components is configured such that the antennas are not in direct contact with the subject. In an embodiment, a wearable components is configured such that at least some of the antennas are not in direct contact with the subject. In an embodiment, each of the plurality of conductive antennas can be used as a transmitting antenna or as a receiving antenna.

In an embodiment, multiple unique orthogonal signals are operatively conducted to one or more transmitting antennas. In an embodiment, a signal generator is used to generate a plurality of unique orthogonal signals, each of which is operatively conducted to a transmitting antenna. In an embodiment, multiple unique orthogonal signals are operatively conducted to one or more transmitting antennas. In an embodiment, a matrix switcher is configured to selectively operatively connect the signal generator's output of any of a plurality of unique orthogonal signals to any antenna that may be used as a transmitting antenna. In an embodiment, a signal processor is used to provide a measurement for each of a plurality of unique orthogonal signals received by each of one or more receive antennas. In an embodiment, a matrix switcher is configured to selectively operatively connect each receiving antenna to an input of the signal processor.

In an embodiment, each transmitting antenna 140 transmits a unique frequency orthogonal signal that is identifiable by the signal processor. In an embodiment, there are multiple devices that are located on the body, each of the multiple devices comprising one or more transmitting antennas 130 and one or more receiving antennas 140. In an embodiment, the transmitting antennas 130 function in such a way that they infuse signals into the subject which are then received by the receiving antennas 140. In an embodiment, one or both of the receiving antennas 140 and transmitting antennas are located internally within the body.

In an embodiment, the sensing apparatus 100 is a band worn on the arm. In an embodiment, the sensing apparatus 100 is an eye mask. In an embodiment, the sensing apparatus 100 is scarf worn around the neck. In an embodiment, the sensing apparatus 100 is a collar. In an embodiment, the sensing apparatus 100 is a bracelet. In an embodiment, the sensing apparatus 100 is worn on the wrist. In an embodiment, the sensing apparatus 100 is formed as goggles or glasses. In an embodiment, the sensing apparatus 100 is worn on a foot or the feet. In an embodiment, the sensing apparatus 100 is an earring or earrings. In an embodiment, the sensing apparatus 100 is a band worn on the legs. In an embodiment, the sensing apparatus 100 is worn on the chest. In an embodiment, the sensing apparatus 100 is worn on the back. In an embodiment, the sensing apparatus 100 is worn in the groin area.

In an embodiment, antennas are formed as three-dimensional objects (or the faces of such three-dimensional objects), examples of which include: cubes, rectangular prisms, triangular prisms, octagonal prisms, tetrahedrons, square pyramids, cylinders and cones. In such embodiment, interleaving in two or more dimensions is possible. For example, 2 mm cubes could be placed e.g., 2 mms apart in a two dimensional grid on a first structure that is, e.g. 1" wide and worn on the wrist, while another layer of similar cubes could be deployed on a second structure. In an embodiment, a large dense array of e.g., alternating transmitters and receivers can interact. Using the mixed signal integrated circuit described above, or another system that can transmit and receive frequency-orthogonal signals, and detect changes in signal interaction, biometric data can be measured by the system.

In an embodiment, each transmitting antenna can be used to transmit a plurality of frequency-orthogonal signals. In an embodiment, the location of transmitting antennas 130 and receiving antennas 140 can be dynamically re-configured, allowing each antenna to operate as either a transmitting antenna or a receiving antenna during any integration period. In an embodiment, an antenna can be used as both a transmitting antenna and a receiving antenna (albeit of different frequency-orthogonal signals) during a single integration period. In an embodiment, two groups of antenna are used as both transmitting antennas and receiving antennas during the same integration period; the first group of antennas has its received signals passed through a high pass filter and are used to transmit only low frequencies, while the second group of antennas has its received signals passed through a low pass filter and transmits only high frequencies.

The transmitting antennas 130 and receiving antennas 140 can be arranged and formed as part of an antenna array including one or more transmitting antennas 130 and one or more receiving antennas 140. Generally, more antennas will lead to collection of more data. However, the placement of antennas so that they provide information related to the biometric data that is to be obtained, and not quantity alone, may lead to improved capability for measurement. In an embodiment, antennas are placed in key locations on or proximate to a body part in order to obtain biometric data. By "proximate" it is generally meant close enough that the placement of the antennas are able to provide information regarding the body part, or on the surface of the skin to obtain biometric data about a body function. In an embodiment, antennas of an array are placed at specific locations where veins and/or arteries are located. In an embodiment, transmit and receive antennas (or transmit and receive antenna groups) are placed on the skin, and the stretching of the skin and movement of subdermal structures causes consequential signal changes used to obtain biometric data. In an embodiment, transmit and receive antennas (or transmit and receive antenna groups) are placed on the skin, and environmental dermal changes are used to obtain biometric data. In an embodiment, machine learning algorithms are used to associate measured signals with biometric data.

In an embodiment, very small transmit and receive antennas are positioned directly on a variety of nearby locations on the body, and can detect relative movement to one another—and that relative movement can be used to obtain biometric data. In an embodiment, antennas are affixed to the hair, hair follicles or skin using small amounts of adhesive.

Figure 3:
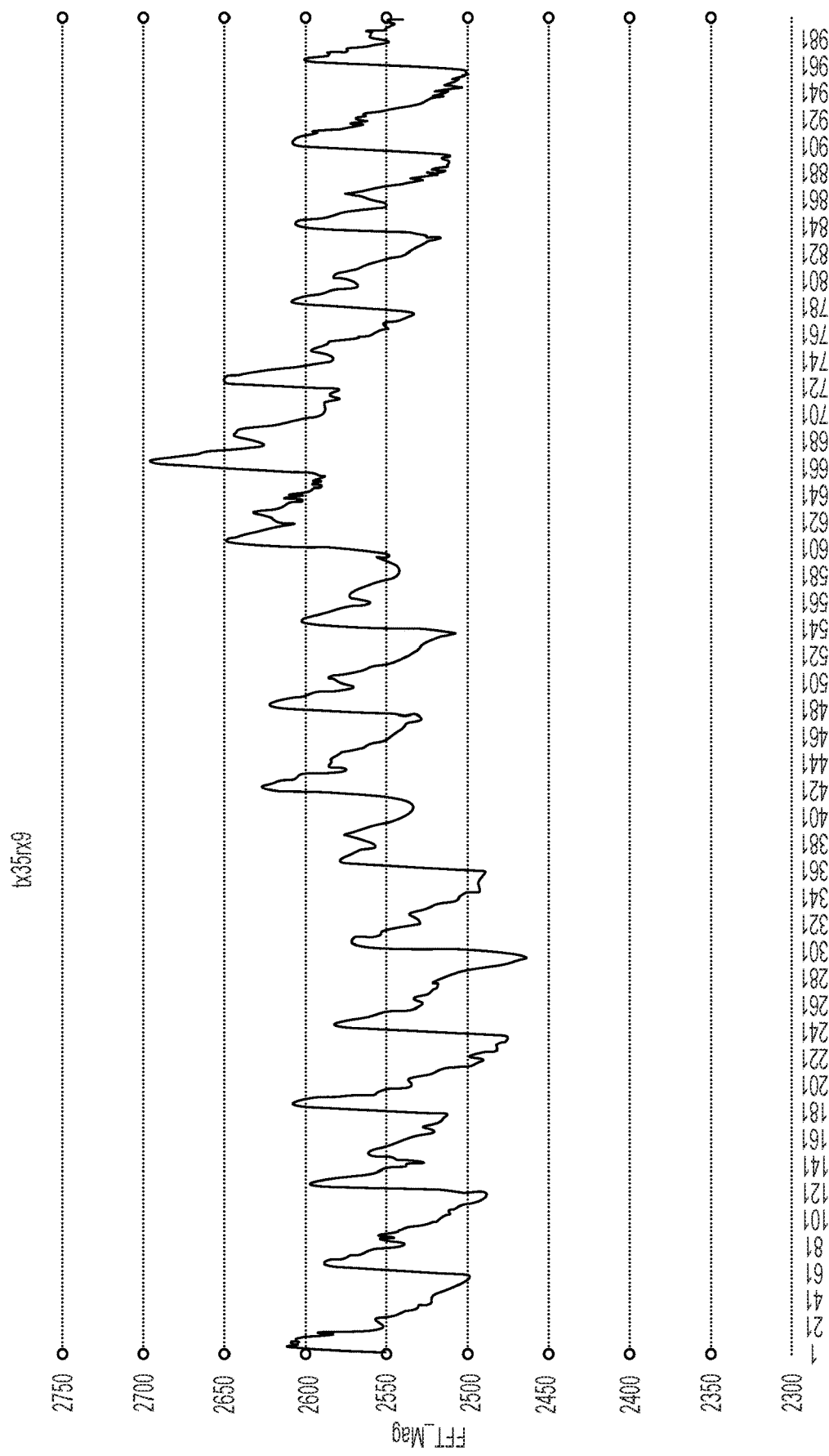
FIG. 3 shows a graph of measured signals received at the receiver.

When in use the amount of signal received from a transmitting antenna at a receiver is measured. Referring to FIG. 3, shown is the measured amount of signal received at a particular receiver during a series of integration periods. The activity indicates that during certain integration periods more signal is being received than at other frames. The measured signal can be indicative of a biological activity. In an embodiment, the measured signal during each frame can be indicative of a biological activity. In an embodiment, the measured signal during a plurality of frames can be indicative of biological activity.

Figure 4:
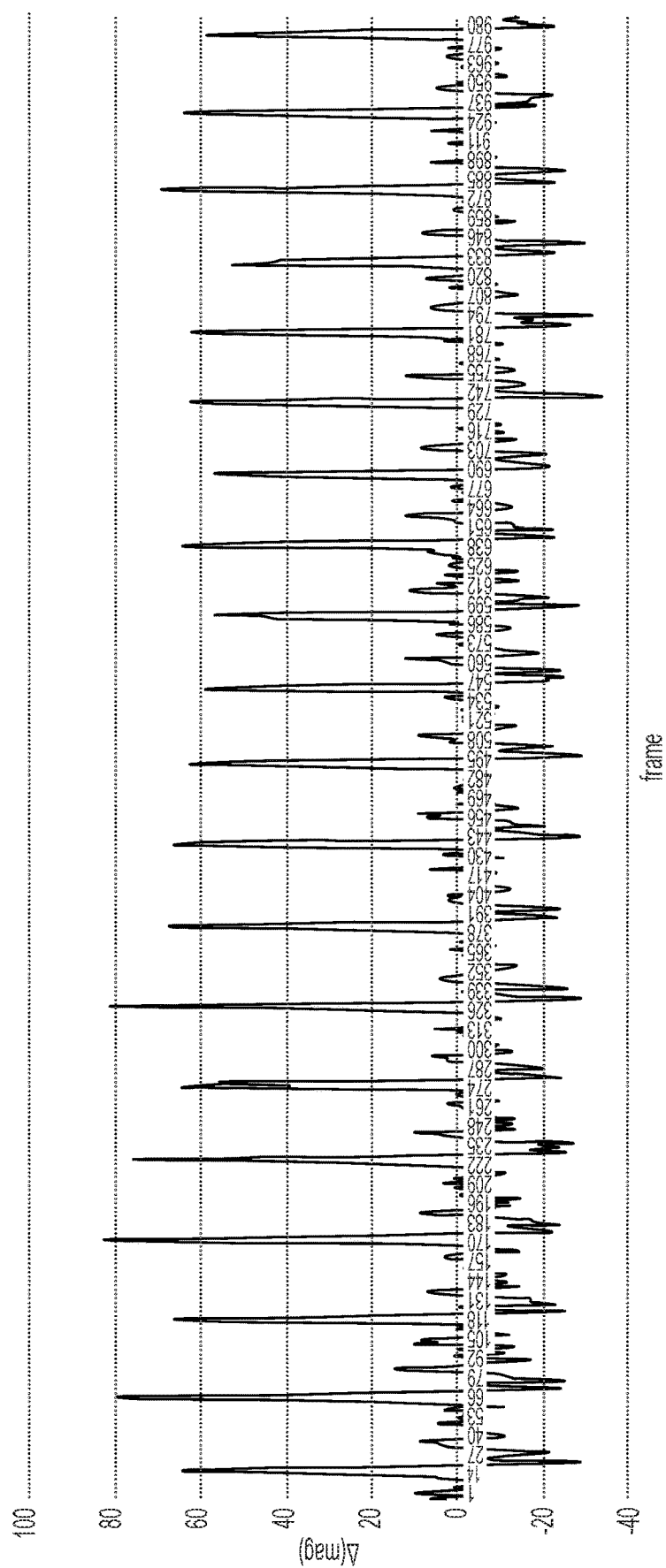
FIG. 4 shows another graph of measured signals received at the receiver.

FIG. 4 is another graph illustrating the measured amount of signal received at a particular receiver during a series of integration periods. In the graph of FIG. 4, the delta between the current and previous received signal is illustrated. This provides a different perspective of the received signal and can make signals indicative of biometric data easier to visualize and use for establishing biometric data.

The measured signal is able to be processed in order to provide biometric data about a person. The biometric data is information that is related to and/or associated with a biological activity. In an embodiment, the biometric data is associated with heart rate. In an embodiment, the biometric data is associated with circulatory activity. In an embodiment, the biometric data is associated with respiratory activity. In an embodiment, the biometric data is associated with dermal activity. In an embodiment, the biometric data is associated with vocal activity. In an embodiment, the biometric data is associated with auditory activity. In an embodiment, the biometric data is associated with gait. In an embodiment, the biometric data is associated with muscle activity. In an embodiment, the biometric data is associated with ocular activity. In an embodiment, the biometric data is associated with eyelid activity. In an embodiment, the biometric data is associated with digestive activity. In an embodiment, the biometric data is associated with the transmission of signal within the body. In an embodiment, the biometric data is associated with particular parts of the body and is used in order to landmark particular parts of the body, for example, particular veins and arteries, such as the superficial palmar arch may be able to provide orientation of a hand relative to a surface. In an embodiment, landmarking particular arteries using a wearable device can permit us to track the wearable device's placement on a body for a period of time.

As discussed above, in order to obtain the biometric data the sensing apparatus 100 is located and/or associated with the person so that received signals can be measured and used by the sensing apparatus 100 in order to provide biometric data. The biometric data may then be used for diagnostic purposes, health related issues, identification and other activities.

While the invention has been particularly shown and described with reference to a preferred embodiment thereof, it will be understood by those skilled in the art that various changes in form and details may be made therein without departing from the spirit and scope of the invention.

The invention claimed is:

1. A biometric sensing apparatus comprising:
   a first antenna supported by a first component, the first component configured to be worn by a subject and to maintain the first antenna in proximity to the subject when the first component is worn;
   a plurality of second antennas supported by a second component, the second component configured to be worn by the subject and to maintain the plurality of second antennas in proximity to the subject when the second component is worn;
   a signal generator operatively connected to the first antenna, the signal generator being configured to generate a first frequency signal on the first antenna;
   a signal processor operatively connected to the plurality of second antennas, the signal processor being configured to process a receive signal received on each of the second antennas during a plurality of integration periods, and for each of the plurality of integration periods and for each of the second antennas to determine a measurement of an amount of the receive signal received corresponding to the first frequency signal using a fast fourier transform; and
   wherein the measurements corresponding to the first frequency signal taken during the plurality of integration periods provides data regarding a biometric of the subject.

2. The biometric sensing apparatus of claim 1, wherein at least one of the first component and the second component comprises a dielectric layer that is configured such that at least one of the first antenna or the plurality of second antennas are separated from the subject by the dielectric layer when the at least one of the first component and the second component is worn.

3. The biometric sensing apparatus of claim 1, wherein when the first antenna is in proximity to the subject the first antenna is touching the subject.

4. The biometric sensing apparatus of claim 1, wherein the second component is made of a rigid material.

5. The biometric sensing apparatus of claim 1, wherein the second component is made of a flexible material.

6. The biometric sensing apparatus of claim 1, wherein the second component is made of rubber or plastic.

7. The biometric sensing apparatus of claim 1, wherein the first component and the second component form a unitary component.

8. The biometric sensing apparatus of claim 1, wherein the first component is adapted to be worn on an arm of the body.

9. The biometric sensing apparatus of claim 1, wherein the biometric of the subject is related to heart activity.

10. The biometric sensing apparatus of claim 1, wherein the biometric of the subject is related to pulmonary activity.

11. The sensing apparatus of claim 1, wherein the biometric of the subject is related to involuntary body activity.

12. The sensing apparatus of claim 1, wherein the biometric of the subject is related to location of a vein or artery.

13. A biometric sensing apparatus comprising:
    a first antenna supported by a first component, the first component configured to be worn by a subject and to maintain the first antenna in proximity to the subject when the first component is worn;

a plurality of second antennas supported by a second component, the second component configured to be worn by the subject and to maintain the plurality of second antennas in proximity to the subject when the second component is worn;

a signal generator operatively connected to each of the plurality of second antennas, the signal generator being configured to generate at least one of a plurality of unique frequency-orthogonal signals on each of the plurality of second antennas during a plurality of integration periods;

a signal processor operatively connected to the first antenna, the signal processor being configured to process a receive signal received on the first antenna during a plurality of integration periods, and for each of the plurality of integration periods to determine a measurement of an amount of the receive signal received corresponding to each of the unique frequency-orthogonal signals using a fast fourier transform; and wherein the measurements corresponding to each of the unique frequency-orthogonal signals during the plurality of integration periods provide data regarding a biometric of the subject.

14. The biometric sensing apparatus of claim 13, the signal processor further being configured to process a second receive signal received on the first antenna during a second plurality of integration periods, and for each of the second plurality of integration periods to determine a measurement corresponding to each of the unique frequency-orthogonal signals; and wherein the measurements corresponding to each of the unique frequency-orthogonal signals during the second plurality of integration periods provide data regarding a biometric of the subject.

15. The biometric sensing apparatus of claim 13, wherein at least one of the first component and the second component comprises a dielectric layer that is configured such that at least one of the first antenna or the plurality of second antennas are separated from the subject by the dielectric layer when the at least one of the first component and the second component is worn.

16. The biometric sensing apparatus of claim 13, wherein when the plurality of second antennas is in proximity to the subject at least one of the plurality of second antennas is touching the subject.

17. The biometric sensing apparatus of claim 13, wherein the second component is made of a rigid material.

18. The biometric sensing apparatus of claim 13, wherein the second component is made of a flexible material.

19. The biometric sensing apparatus of claim 13, wherein the second component is made of rubber or plastic.

20. The biometric sensing apparatus of claim 13, wherein the first component and the second component form a unitary component.

21. The biometric sensing apparatus of claim 13, wherein the first component is adapted to be worn on an arm of the body.

22. The biometric sensing apparatus of claim 13, wherein the biometric of the subject is related to heart activity.

23. The biometric sensing apparatus of claim 13, wherein the biometric of the subject is related to pulmonary activity.

24. The sensing apparatus of claim 13, wherein the biometric of the subject is related to involuntary body activity.

25. The sensing apparatus of claim 13, wherein the biometric of the subject is related to location of a vein or artery.

* * * * *